(12) United States Patent
Ouwerkerk et al.

(10) Patent No.: US 11,197,623 B2
(45) Date of Patent: Dec. 14, 2021

(54) SYSTEM FOR IMPROVING SLEEP EFFECTIVENESS OF A USER

(71) Applicant: KONINKLIJKE PHILIPS N.V., Eindhoven (NL)

(72) Inventors: Martin Ouwerkerk, Culemborg (NL); Marc Nieuwhof, Eindhoven (NL); Navin Hemchand Natoewal, Utrecht (NL)

(73) Assignee: Koninklijke Philips N.V., Eindhoven (NL)

( * ) Notice: Subject to any disclaimer, the term of this patent is extended or adjusted under 35 U.S.C. 154(b) by 388 days.

(21) Appl. No.: 16/092,627

(22) PCT Filed: Apr. 7, 2017

(86) PCT No.: PCT/EP2017/058360
§ 371 (c)(1),
(2) Date: Oct. 10, 2018

(87) PCT Pub. No.: WO2017/178359
PCT Pub. Date: Oct. 19, 2017

(65) Prior Publication Data
US 2019/0117110 A1    Apr. 25, 2019

(30) Foreign Application Priority Data
Apr. 12, 2016   (EP) .................................... 16164795

(51) Int. Cl.
*A61B 5/0531*   (2021.01)
*A61B 5/00*     (2006.01)
(Continued)

(52) U.S. Cl.
CPC ............ *A61B 5/0531* (2013.01); *A61B 5/165* (2013.01); *A61B 5/4815* (2013.01); *A61B 5/681* (2013.01); *A61B 5/7225* (2013.01); *A61B 5/0533* (2013.01)

(58) Field of Classification Search
CPC ....... A61B 5/0531; A61B 5/165; A61B 5/681; A61B 5/7225; A61B 5/4815; A61B 5/0533
See application file for complete search history.

(56) References Cited

U.S. PATENT DOCUMENTS

2007/0118054 A1* 5/2007 Pinhas ................. A61B 5/4815
                                                    600/587
2014/0329214 A1* 11/2014 Bitoun ............... A61B 5/02055
                                                    434/262
(Continued)

FOREIGN PATENT DOCUMENTS

| WO | 2015054134 A1 | 4/2015 |
| WO | 2015082231 A2 | 6/2015 |
| WO | 2015189107 A1 | 12/2015 |

OTHER PUBLICATIONS

Lee-Chiong, J., "Sleep: A Comprehensive Handbook", Wiley & Sons, Hoboken, NJ, 2005.
(Continued)

*Primary Examiner* — Devin B Henson
*Assistant Examiner* — Joseph A Tombers (57) ABSTRACT

The present invention relates to a system for improving sleep effectiveness of a user. The present invention further relates to a signal processing device (10) for processing skin conductance data of a user, the device comprising: an input unit (11) for receiving a skin conductance data signal indicative of a skin conductance of the user; a segmentation unit (12) for segmenting the skin conductance data signal into a plurality of epochs; a peak detection 5 unit (13) for
(Continued)

detecting peaks in the skin conductance data signal; a calculation unit (14) for calculating a sum of rising edge amplitudes of the detected peaks per epoch; an analysis unit (15) configured to classify the user into an emotional state based on a transient behavior of said sums of rising edge amplitudes per epoch during the course of a day, wherein the analysis unit is configured to classify the user into an unhealthy tired state when the sum of 10 rising edge amplitudes per epoch increases during the course of the day; and/or to classify the user into a healthy tired state when the sum of rising edge amplitudes per epoch decreases during the course of the day; and an output unit configured to output an output signal indicative of said emotional state. The present invention further relates to a corresponding method and computer program implementing such a method.

20 Claims, 6 Drawing Sheets

(51) Int. Cl.
*A61B 5/16* (2006.01)
*A61B 5/0533* (2021.01)

(56) References Cited

U.S. PATENT DOCUMENTS

| | | | |
|---|---|---|---|
| 2015/0245777 A1* | 9/2015 | Torre | A61B 5/11 600/301 |
| 2016/0262690 A1* | 9/2016 | Chen | A61B 5/02405 |
| 2016/0270718 A1* | 9/2016 | Heneghan | G16H 50/30 |

OTHER PUBLICATIONS

Machado-Moreira, C. et al., "Sudomotor responses from glabrous and non-glabrous skin during cognitive and painful stimulations following passive heating", Acta physiologica, vol. 204, issue 4, pp. 571-581, Apr. 2012.

Ouwerkerk, M. et al., "Wireless multi sensor bracelet with discreet feedback", Proceedings of the 4th Conference on Wireless Health, p. 6, 2013.

P. Corkum, F. et al., "A Framework for the Assessment and Treatment of Sleep Problems in Children with Attention-Deficit/Hyperactivity Disorder", Pediatr. Clin. N. Am 58 (2011) 667-683.

A. G. Bonomi, G. Plasqui, A. H. C. Goris, K. R. Westerterp, "Improving assessment of daily energy expenditure by identifying types of physical activity with a single accelerometer", Journal of Applied Physiology 107 (2009), 655-661.

Westerink, J.H.D.M., Ouwerkerk, M., de Vries, J.J.G., De Waele, S., van den Eerenbeemd, J., van Boven, M. 2009. "Emotion measurement platform for daily life situations", Proceedings vol. I, International Conference on Affective Computing & Intelligent Interaction, ACII (Sep. 2009), Amsterdam, The Netherlands, 217-222.

Ming-Zher Poh, N.C. Swenson, R.W. Picard, "A Wearable Sensor for Unobtrusive, Long-Term Assessment of Electrodermal Activity", IEEE Transactions on Biomedical Engineering, 57 (2010) 1243-1252.

Caruso, Claire, "Running on Empty: Fatigue and Healthcare Professionals", medscape.com, Aug. 2012.

Kirchbaum, C, Pirke, K.-M., and Hellhammer, D.H., "The 'TrierSocial Stress test'—A Tool for Investigating Psychobiological Stress Responses in a Laboratory Setting", Neuropsychobiology 28 (1993) 76-81.

"F.Lux—Software to Make Your Life Better", https://justgetflux.com/, accessed Oct. 9, 2018.

Muzet, A et al, "REM sleep and ambient temperature in man", Int. J. of Neuroscience 18 (1983) 117-125.

Ouwerkerk, M. e al., "Discreet tension indicator DTI-2 skin conductance wristband technical construction description", Technical Note PR-TN 2012/00558, Philips Research Europe, Issued Feb. 2013.

* cited by examiner

SYSTEM FOR IMPROVING SLEEP EFFECTIVENESS OF A USER

CROSS-REFERENCE TO PRIOR APPLICATIONS

This application is the U.S. National Phase application under 35 U.S.C. § 371 of International Application No. PCT/EP2017/058360, filed on 7 Apr. 2017, which claims the benefit of European Patent Application No. 16164795.3, filed on 12 Apr. 2016. These applications are hereby incorporated by reference herein.

FIELD OF THE INVENTION

The present invention relates to a system for improving sleep effectiveness of a user. The present invention further relates to a signal processing device and method for processing skin conductance data of a user as well as a corresponding computer program implementing such a method.

BACKGROUND OF THE INVENTION

Sleep disorders are reported to have a prevalence between 10 and 33 percent of the population as described in "Sleep: A Comprehensive Handbook", Lee-Chiong, John Wiley & Sons, Hoboken, N.J., USA, 2005. Sleep deprivation can impair job performance and increase risk for worker errors and injuries.

In this context, WO 2015/054134 A1 discloses a fatigue monitoring and management system. The system comprises a non-obstructive sleep sensor to generate objective sleep measures of the user. Based on these sleep measures, the system determines a fatigue state of the user. It is proposed that the system acts as a personalized fatigue and sleep analyzer capable of providing a person with a personalized and scientifically valid 'go to sleep' time that will maximize sleep and minimize fatigue for better health and performance.

WO 2015/082231 A2 discloses a processor for processing skin conductance data and a device for detecting at least one stage of burnout and/or chronic fatigue syndrome of a living being.

SUMMARY OF THE INVENTION

It is an object of the present invention to provide a system which supports a user in having an effective restful sleep. It is a further objective to provide a signal processing device and method which enable such a system.

In a first aspect of the present invention signal processing device for processing skin conductance data of a user is presented that comprises an input unit for receiving a skin conductance data signal indicative of a skin conductance of the user; a segmentation unit for segmenting the skin conductance data signal into a plurality of epochs; a peak detection unit for detecting peaks in the skin conductance data signal; a calculation unit for calculating a sum of rising edge amplitudes of the detected peaks per epoch; an analysis unit configured to classify the user into an emotional state based on a transient behavior of said sums of rising edge amplitudes per epoch during the course of a day, wherein the analysis unit is configured to classify the user into a 'unhealthy tired' state when the sum of rising edge amplitudes per epoch increases during the course of the day; and/or to classify the user into a 'healthy tired' state when the sum of rising edge amplitudes per epoch decreases during the course of the day; and an output unit configured to output an output signal indicative of said emotional state.

In a further aspect of the present invention a system for improving sleep effectiveness of a user is presented that comprises the aforementioned signal processing device for processing the skin conductance data and an interface for providing the user with a sleep preparatory advice based on the emotional state of the user.

In a further aspect of the present invention a method, in particular a computer-implemented method, for processing skin conductance data of a user is presented, the method comprising the steps of: obtaining skin conductance data signal indicative of a skin conductance of the user; segmenting the skin conductance data signal into a plurality of epochs; detecting peaks in the skin conductance data signal; calculating a sum of rising edge amplitudes of the detected peaks per epoch; classifying the user into an emotional state based on a transient behavior of said sum of rising edge amplitudes per epoch during the course of a day, wherein the user is classified into an 'unhealthy tired' state when the sum of rising edge amplitudes per epoch increases during the course of the day; and/or into a 'healthy tired' state when the sum of rising edge amplitudes per epoch decreases during the course of the day.

Preferred embodiments of the invention are defined in the dependent claims. It shall be understood that the claimed system, method and computer program can have similar and/or identical preferred embodiments as the claimed device and as defined in the dependent claims.

After a busy and/or emotional day it is often hard to fall asleep. Hence, even when going to bed early, for example at a time as suggested by WO 2015/054134 A1, a person may stay awake for some time and when finally falling asleep may not reach an effective restful sleep level.

The inventors have thus identified that there is a need to diminish sleep onset time, optimize sleep quality and restful sleep duration. The solution presented herein provides a signal processing device which classifies a user into a first emotional state, referred to as an unhealthy tired state, and/or a second emotional state, referred to as a healthy tired state, based on the skin conductance data of a user. Based on this output of the signal processing device, the proposed system for improving sleep effectiveness of a user can provide the user with an appropriate sleep preparatory advice aimed at preparing the user to fall asleep fast and advantageously have a sleep period containing deep sleep stages. The sleep preparatory advice can also be referred to as wind down advice or sleep preparation advice. After a proper sleep preparation or wind down, the sleep onset time reduces such that the user may quickly reach an effective restful sleep. The proposed solution thus supports the sleep preparation of a user based on a nature or type of the emotional state. The proposed system can also be referred to as an advisory, sleep-preparation or pre-sleep coaching system which supports a user in diminishing sleep onset time, optimizing sleep quality, and/or sleep duration.

The proposed signal processing device comprises an input unit for receiving a skin conductance data signal indicative of a skin conductance of the user. The skin conductance data signal can be understood as the output of a skin conductance sensor applied to the user. An advantage of a skin conductance measurement is that, in contrast an EEG (electroencephalogram) based measurement wherein electrodes have to be arranged on the users head, it is an unobtrusive measurement. A skin conductance measurement can also be referred to as a galvanic skin conductance (GSR) measurement or electrodermal activity (EDA) measurement. A skin conductance sensor can basically be worn on all body locations. Psychological sweating can occur all of the body, as indicated in Machado-Moreira et al., "Sudomotor responses from glabrous and non-glabrous skin during cognitive and painful stimulations following passive heating", Acta Physiol, 204, 571-581, 2012. Skin conductance sensors are a good means to detect changes in sweating. The conductance increases when sweat responses occur, because sweat contains ions making it a conductive medium. A skin conductance sensor can be easily attached to the user, e.g. as part of a watch, a separate wristband or body sensor in the kind of a belt.

The segmentation unit is configured to segment the skin conductance data signal into a plurality of epochs. An epoch as used herein can refer to a time segment, time unit or time period. The segmentation unit can thus divide the received skin conductance signal into time segments for subsequent analysis. The peak detection unit is configured to detect peaks in the received skin conductance signal. Peak detection methods as such are generally known in the art. For example, a peak can refer to a local maximum, in particular a local maximum which exceeds a predetermined threshold. It has been found that a peak in the skin conductance signal can be indicative of a response to an emotional stimulus. The height of the peak can in turn be indicative of the strength of the response to the stimulus. A peak which has been determined by the peak detection unit can also be referred to as a skin conductance response (SCR). The calculation unit is configured to calculate the respective sums of rising edge amplitudes of the detected peaks per epoch. In other words, for each epoch the heights of the rising edges of the determined peaks can be accumulated to obtain a sum value for each epoch. Preferably, the heights are determined with respect to an average, in particular a moving average, of the received skin conductance data signal which can be referred to as a skin conductance level (SCL). The heights or amplitudes of the rising edges can also be determined with respect to a baseline of the skin conductance data signal. A baseline can refer to the skin conductance data signal with peaks removed. The term rising edge amplitude can thus refer to a difference between the value of the skin conductance data signal at the respective peak as the upper value and the baseline or average of the skin conductance data signal as the lower value. The sum of rising edge amplitudes per epoch or cumulative rising edge heights per epoch can thus be indicative of a cumulative emotional load experienced by the user in said epoch.

The analysis unit in turn evaluates a transient behavior of the respective sums of rising edge amplitudes per epoch during the course of the day. The transient behavior is descriptive of how the sum of rising edge amplitudes evolves over time during the course of the day. In other words, the transient behavior is descriptive of a change of the sum of rising edge amplitudes per epoch over time. The analysis unit discriminates between at least two fatigue patterns. The inventors have found that the different emotional fatigue patterns can be determined based on a change in the responsiveness to stressors over time. The first type of fatigue pattern, referred to as the 'unhealthy tired' state, is characterized by an increased response to stressors, whereas the second type of fatigue pattern, referred to as the 'healthy tired' state, is characterized by a diminished response to stressors. It has been found that these states can be distinguished by the analysis unit, wherein the analysis unit is configured to classify the user into the 'unhealthy tired' state when the sum of rising edge amplitudes per epoch increases during the course of the day; and/or to classify the user into the 'healthy tired' state when the sum of rising edge amplitudes per epoch decreases during the course of the day.

In particular, it has been found that in the unhealthy tired state an increase in the skin conductance response peak heights indicates a stronger emotional response to stimuli. A person experiencing this state of fatigue may be bound to be more sensitive to what is happening to them. Such an increased sensitivity generally results in a more irritable mood. Little annoyances already can cause strong outbursts of anger. The increased emotional response to stimuli may find its cause in failure to recruit top-down prefrontal regions involved in emotion regulation. It has been found that only a challenging attention task and not simple mental tasks may cause this. Furthermore, exposure to negative emotional triggers may cause of this type of mental or emotional fatigue.

By contrast, the second fatigue pattern can be seen as indicative of a lessened response to stimuli. Especially during routine tasks such an effect is to be expected. Due to the secreted cortisol caused by subsequent stressors the responsiveness to stressors is dampened. It is perfectly healthy to quit responding to new stressors because of this hormonal response, which can also be seen as drowsiness, or sleepiness. This type of state is thus designated as 'healthy tired'.

In an embodiment, the analysis unit can be further configured to classify the user into a 'not tired' state when the sum of rising edge amplitudes per epoch remains stable during the course of the day and exceeds a first threshold; and/or to classify the user into an 'under-stimulated' state of the user when the sum of rising edge amplitudes per epoch remains below said first threshold during the course of the day. If the responsiveness to stressors has remained more or less the same during the entire day a user apparently was able to deal with the emotions in a balanced way. This emotional state at the end of the day can therefore be designated as 'not tired'. However, when the responsiveness to stressors has been below the first threshold throughout the day a user can be seen as under-stimulated, or even bored. This state can therefore be designated as 'under-stimulated'. Hence, according to this embodiment, the analysis unit can be configured to analyze the skin conductance data and to classify an emotional state of the user based on the measured skin conductance data into one or more of an under-stimulated state, a not tired state, a healthy tired state and an unhealthy tired state. Optionally, a high average skin conductance level or skin conductance level above a second threshold can also be used to discriminate the healthy tired state, e.g. from a person being in an under-stimulated state or in a setting with little emotional stimuli. It has been found that a setting with little emotional stimuli results in a low sum of rising edge amplitudes, but can also result in a significant lowering of the skin conductance level. Regarding the healthy tired state it has been found that if a person's responsiveness to stressors is strongly diminished as a result of fatigue, an increased effort to do his or her tasks can cause an increase in sweating and thus in the skin conductance level. Hence, in addition or in the alternative to classifying a user into a healthy tired state when the sum of rising edge amplitudes per epoch decreases during the course of the day, the analysis unit can be configured to classify the user into a healthy tired state when an average or a baseline value of the skin conductance data signal per epoch increases during the course of the day. An average value per epoch can be taken as a discriminating parameter when skin conductance responses are (almost) absent. A baseline value can refer to the skin conductance data signal with peaks removed. Based on which of the aforementioned states a person is in, e.g. in an under-stimulated state, a not tired state, a healthy tired state and an unhealthy tired state, the sleep improvement system at the end of the waking day computes an advice to optimize the sleep effectiveness.

In an embodiment, the skin conductance data signal is indicative of a full day measurement of the skin conductance of the user. Preferably, the signal processing device evaluates a full day signal trace of the skin conductance data of the waking day. For example, the skin conductance signal is obtained while the user wears a watch-like skin conductance sensor or smart watch, in particular during daytime. An advantage is that in this case no sensor device has to be worn at night, hence no such device disturbs the user at night.

In an embodiment, the analysis unit is configured to classify the user into said emotional state based on a comparison the sum of rising edge amplitudes of one or more epochs at a beginning of the day with the sum of rising edge amplitudes of one or more epochs at an end of the day. It is thus also possible to evaluate only some epochs of the day. By comparing the one or more epochs of the beginning of the day with one or more epochs of the end of the day, the required comparison of how the sums of rising edge amplitudes change over time during the course of the day can be obtained. For example, a first epoch can be measured at the beginning of the working day and a second epoch can be measured at the end of the working day. An advantage of this embodiment is reduced power consumption because system components can be shut off or set into a low power mode between the epochs used for classification.

In an embodiment, an epoch can have a duration between 10 and 90 minutes, preferably between 20 and 60 minutes, preferably between 25 and 45 minutes, preferably a duration of 30 minutes. For example, the skin conductance data signal is segmented into multiple, advantageously non-overlapping, epochs of about 30 minutes. An advantage of these epoch durations is that they provide a sufficient averaging effect but at the same time enable an analysis of a transient behavior or change of the sums of rising edge amplitudes per epoch over a period of a few hours, thus over a period of time which covers several epochs.

In an embodiment, the system for improving sleep effectiveness of a user further comprises a skin conductance sensor for measuring skin conductance data of a user. The skin conductance sensor can comprise at least two electrodes adapted to be applied to a skin surface and electronic circuitry for measuring a conductivity and/or resistance between said at least two electrodes. Alternatively or in addition, the signal processing device of the system for improving sleep effectiveness may also receive the skin conductance data signal from a database, where the skin conductance signal has been stored. In particular, it should be understood that the proposed system can also be implemented as a distributed system wherein the skin conductance sensor, the processing device and/or the interface for providing the user with the sleep preparatory advice are not necessarily implemented as one physical entity.

In an embodiment, the system for improving sleep effectiveness of a user is at least in part configured as a wearable device. A wearable device as used herein can particularly refer to a smart watch, smart phone, wrist band, chest-band, an activity tracker and the like. Advantageously, the wearable device comprises a skin conductance sensor configured to contact a skin of the user when worn by the user.

In an embodiment, the system for improving sleep effectiveness of a user is further configured to provide said sleep preparatory advice to the user a predetermined time interval before bedtime, preferably at the end of the day, preferably several hours prior to sleep. An advantage of this embodiment is that the user can make an informed decision for example on how much time will likely be required for an appropriate sleep preparation or wind down and plan the remainder of the day accordingly. The bedtime can be provided by a user for example via a user interface, may be obtained from a schedule or may be a recommended 'go to sleep' time as suggested in WO 2015/054134 A1.

In an embodiment, the sleep preparatory advice comprises one or more of a period of low stimuli, a relaxing activity, physical activity, calming music, provision of scents, dimmed lighting, and/or lighting having a low color temperature. Thereby, the provided sleep preparatory advice can advantageously support the process that stress induced cortisol dies down. Moreover, the sleep preparatory advice may be adapted to stimulate melatonin production. In consequence the user may fall asleep more quickly and have an effective restful sleep. Advantageously, the sleep preparatory advice can be set according to user preferences. It should be noted that the sleep preparatory advice can be presented in different forms. For example, the sleep preparatory advice can be provided to the user as a recommendation on the user interface, for example on the display of a smartphone of the user in form of a recommended action. However, the sleep preparatory advice can also be directly provided to the user in that the system for improving sleep effectiveness controls one or more external entities.

In an embodiment, the system for improving sleep effectiveness of a user can thus be further configured to control one or more of a light source, an audio unit and/or a scent dispenser based on the emotional state of the user. For example, a light source may be dimmed based on the emotional state of the user in compliance with a sleep preparatory advice of having dimmed light. It has been found that the wind down or sleep preparation can advantageously take place in a setting with dimmed light, preferably less than 250 lux, and/or in a setting with light having a low color temperature, preferably below 2700K, in particular in a setting where blue light in the range of for example 460-480 nm wavelength is virtually absent, and/or in a setting with light with a spectrum with low intensity around 480 nm. It has further been found that the wind down can advantageously take place when scents such as lavendin, lavender and/or valerian are provided to the user. Hence, a corresponding advice can be provided to the user. An advantage of this embodiment is that the wind down or sleep preparation process can be automatically controlled by the system, e.g. the system controls the lighting accordingly, such that the user can be automatically prepared for a restful night. It is also possible to provide one or more modalities which support the wind down such as scents, audio or light adjustments at a subconscious level. An advantage of this approach is that the wind down or sleep preparation of the user can be supported without evoking a feeling of being forced to wind down.

In an embodiment, the system for improving sleep effectiveness of a user said sleep preparatory advice comprises a duration of a recommended wind down or sleep preparation period, wherein the duration of the wind down period is determined based on the emotional state of the user. In particular, the length or duration of the wind down or sleep preparation period is dictated by the time it takes for emotion induced cortisol to be removed from the body. For example, if the analysis unit has classified the user as 'unhealthy tired' the system may recommend a wind down period of 2 hours before sleeping, whereas, if the analysis unit has classified the user as 'healthy tired', a wind down period of 30 minutes or less may be sufficient. An advantage of this embodiment is that the wind down period is tailored to the user's actual needs.

In an embodiment, the system for improving sleep effectiveness of a user can further comprise a sleep assessment sensor and the system can be configured to adjust the sleep preparatory advice based on a feedback signal from said sleep assessment sensor. A sleep assessment sensor may monitor a person while sleeping. Hence, additional information can be obtained, such as sleep duration, sleep stages in particular regarding the length and amount of deep sleep stages and the number of sleep interruptions. Deep sleep stages have been found to be most refreshing. Exemplary devices that can be used as a sleep assessment sensor include but are not limited to the Philips Discreet Tension Indicator wristband and further devices of the Philips WeST wearable sensor technologies. An advantage of this embodiment is that a sleep assessment sensor can thus provide feedback about the effectiveness of a sleep preparatory advice previously provided to the user. In consequence, the system for improving sleep effectiveness of a user may adjust its future sleep preparatory advice to be provided to the user based thereon. Advantageously, the system for improving sleep effectiveness can be a self-learning system that adapts the sleep preparatory advice, for example the length and type, based on which previously provided sleep preparatory advice led to an effective restful sleep.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
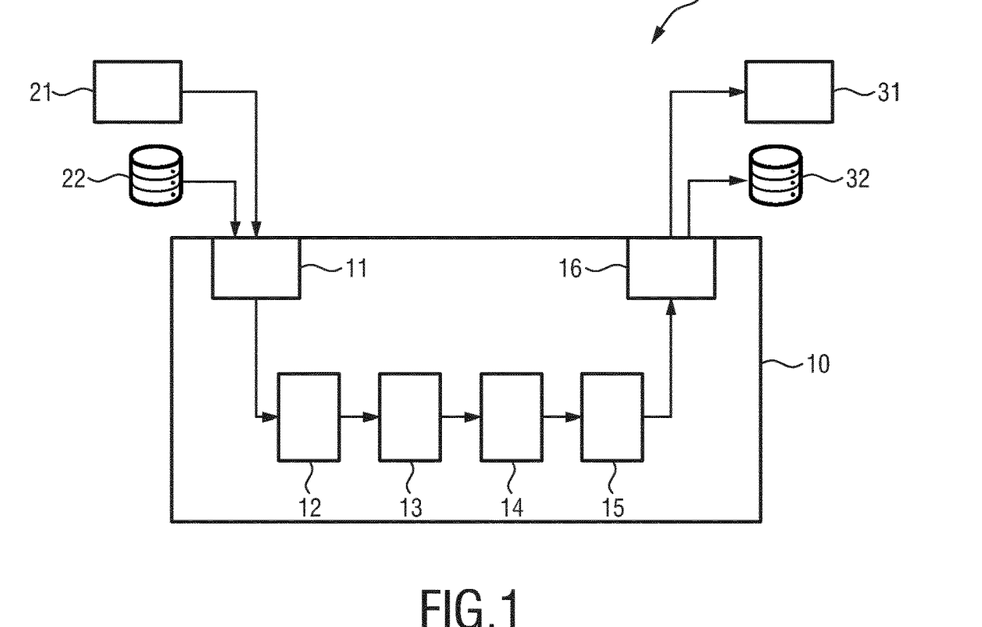
FIG. 1 shows a schematic diagram of a first embodiment of a system for improving sleep effectiveness of a user which comprises a signal processing device for processing skin conductance data of a user.
Figure 3:
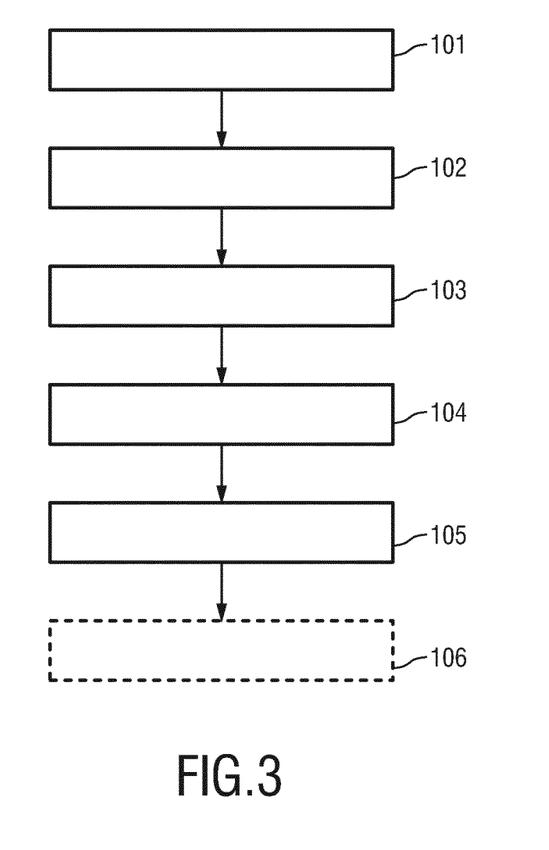
FIG. 3 shows an exemplary embodiment of a method for processing skin conductance data of a user.

FIG. 1 shows a schematic diagram of a first embodiment of a system 1 for improving sleep effectiveness of a user. In this embodiment, the system 1 comprises a signal processing device 10 for processing skin conductance data of a user, a skin conductance sensor 21 for measuring the skin conductance data of the user, and an interface 31 for providing the user with a sleep preparatory advice based on an emotional state of the user. The processing method 100 corresponding to the signal processing device 10 shown in FIG. 1 is illustrated in FIG. 3.

A quantification of the cumulative physical and/or emotional impact of the waking part of a day has now become feasible through the advent of wearable sensors. For example, a physical impact can reliably be measured with a device such as the Philips Directlife token. A quantification of an emotional impact, in particular of the waking part of a day, has come within reach through the advent of wearable skin conductance sensors such as the Philips Discreet Tension Indicator wristband. The Discreet Tension Indicator (DTI-2) wristband is described in Ouwerkerk, M. et al.: "Wireless multi sensor bracelet with discreet feedback", Proceedings of the 4th Conference on Wireless Health, p. 6, 2013, which is incorporated herein by reference.

Referring to FIG. 1, the signal processing device 10 according to an aspect of the present invention comprises an input unit 11 for receiving a skin conductance data signal indicative of a skin conductance of the user; a segmentation unit 12 for segmenting the skin conductance data signal into a plurality of epochs; a peak detection unit 13 for detecting peaks in the skin conductance data signal; a calculation unit 14 for calculating a sum of rising edge amplitudes of the detected peaks per epoch; an analysis unit 15 configured to classify the user into an emotional state based on a transient behavior of said sums of rising edge amplitudes per epoch during the course of a day. Preferably, the analysis unit is further configured to classify the user into an unhealthy tired state when the sum of rising edge amplitudes per epoch increases during the course of the day; and/or to classify the user into a healthy tired state when the sum of rising edge amplitudes per epoch decreases during the course of the day. The processing device 10 preferably further comprises an output unit 16 configured to output an output signal indicative of said emotional state.

As an alternative or in addition to the skin conductance sensor 21, the skin conductance data signal may also be provided to the signal processing unit 10 from a first data base 22.

Correspondingly, as an alternative or in addition to the interface 31, the output signal of the signal processing unit 10 indicative of the emotional state may also be provided to a second data base 32. The first database 22 and second database 32 can also refer to the same database.

Figure 2:
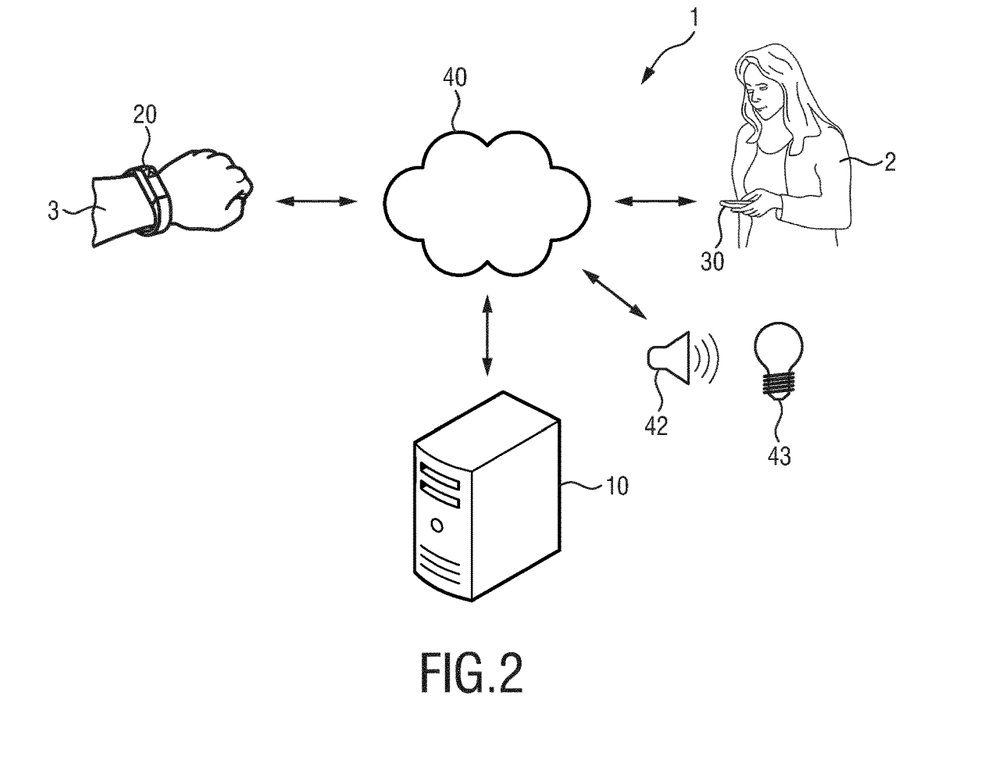
FIG. 2 shows a further embodiment of a system for improving sleep effectiveness of a user.

FIG. 2 illustrates an advantageous embodiment of a system 1 for improving sleep effectiveness of a user 2. In this example, the system 1 is implemented as a distributed system, comprising a wearable device 20, a signal processing device 10 and a user interface device 30 such as a smartphone. Hence, the system is not necessarily implemented as one physical entity. Instead, the devices may feature wired or wireless communication interfaces for interconnectivity as indicated by cloud 40 and thereby are configured to work together as a system 1 for improving sleep effectiveness of the user 2.

In the shown embodiment, the wearable device 20 is a wristband comprising a skin conductance sensor 21 for measuring a skin conductance of the user 2. For example, the wearable device 20 can be a Philips Discreet Tension Indicator wristband. A corresponding device will be described in more detail further below with reference to FIG. 8.

As shown in FIG. 2, the interface 31 for providing the user 2 with the sleep preparatory advice is implemented by means of a smartphone 30 of the user 2. An advantage of this embodiment is that there is no need for the user to carry an additional device and the high quality interface of the smartphone can be used. For example, an app can be provided on the smartphone 30 as the interface 31 for providing the user with the sleep preparatory advice.

It should be noted that the functionality of the processing device 10 can be implemented a dedicated hardware element or also as a cloud based service. An advantage of such an embodiment is that potentially complex calculations do not have to be performed on a mobile device with limited processing power and power supply. Alternatively, the processing device 10 can also form part of the wearable device 20 or of the smartphone 30 or other type of user interface device. Moreover, all system components may also be implemented in just one device such as a smart watch.

Advantageously, the system 1 is further configured to control one or more of a light source 43, an audio unit 42 and/or a scent dispenser based on the emotional state of the user 2. It is also possible that the sleep preparatory advice is solely presented by means of one or more of such devices which may then serve as the interface 31 for providing the user with the sleep preparatory advice.

Optionally, the wearable device 20 can also be used as the sleep assessment sensor. Hence, the system can be further configured to adjust the sleep preparatory advice based on a feedback signal from said sleep assessment sensor. It will be understood that alternatively or in addition other sleep assessment sensors may be used.

FIG. 3 shows an exemplary embodiment of a method 100 for processing skin conductance data of a user. In a first step 101, a skin conductance data signal indicative of a skin conductance of the user is obtained. Obtaining a skin conductance data signal can also refer to receiving the skin conductance data signal from a data base. In a second step 102, the skin conductance data signal is segmented or divided into a plurality of epochs. In a third step 103, peaks in the skin conductance data signal are detected. It should be noted that the steps 102 and 103 can also be performed in different order or even in parallel. In a fourth step 104, a sum of rising edge amplitudes of the detected peaks per epoch is calculated. In a fifth step 105, the user is classified into an emotional state based on a transient behavior of said sum of rising edge amplitudes per epoch during the course of a day. Preferably, the user is classified into an unhealthy tired state when the sum of rising edge amplitudes per epoch increases during the course of the day; and/or a healthy tired state when the sum of rising edge amplitudes per epoch decreases during the course of the day. In an optional further step 106, the user is provided with a sleep preparatory advice based on the emotional state of the user as determined in step 105.

Figure 4A:
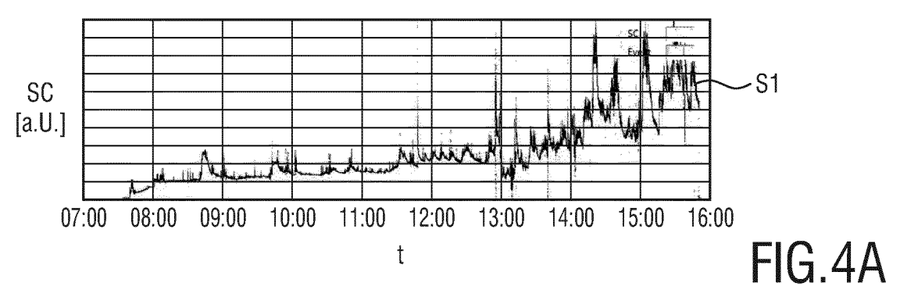
FIG. 4A shows an exemplary skin conductance data signal indicative of an unhealthy tired state.

FIG. 4A shows an exemplary skin conductance data signal S1 indicative of an 'unhealthy tired' state of the user towards the end of the day. The horizontal axis denotes the time t of the day, whereas the vertical axis denotes the skin conductance SC. The unit of the skin conductance can be given in micro Siemens [µS]. The skin conductance data signal S1 in this embodiment represents a working day from about 7:30 AM to 4:00 PM. The data represents the sensor output of a full workday of a driving license examiner. As can be seen from the skin conductance trace S1, a skin conductance peak density, for example the number of peaks per 30 minutes, goes up and also an average peak height increases at the end of the workday.

The proposed signal processing device (10 in FIG. 1) receives a skin conductance trace S1 as shown in FIG. 4A as an input and segments the signal into a plurality of epochs. Each epoch thus represents a time segment of the signal of a predetermined duration, for example 30 or 50 minutes. For each epoch, the peak detection unit 13 detects the peaks in the signal with a peak detection algorithm. The number of peaks can also be referred to as a number of skin conductance responses (SCR). In order to qualify as an SCR, the peak height may have to exceed a threshold. The threshold can be set as a percentage of a skin conductance level (SCL), which can be seen as a baseline under the SCR or a baseline of skin conductance data signal. Preferably, the threshold value can be between 2 and 10 percent of the SCL, for example 5 percent of the SCL. Based thereon, the calculation unit 14 calculates the sum of rising edge amplitudes of the detected peaks per epoch. Of the detected SCR the respective peak heights can be determined from the rising edges. This can also be referred to as rising edge amplitude of the detected peaks. The value may again be given in micro Siemens.

In an embodiment, in an optional pre-processing step which may also be performed by the signal processing device 10, the raw skin conductance signal may be cleaned from motion artifacts, and optionally smoothing can be applied to get rid of high frequency noise, such as 50/60 Hz mains noise.

Regarding an exemplary implementation the peak detection, a first derivative from the skin conductance signal can be taken. Upon a zero crossing from negative to positive it can assumed that a peak onset has been detected. It has been found that SCRs have rise times of the order of one second or more. Hence, a subsequent zero crossing of the first derivative that occurs within one second may not be considered as a valid peak and can be discarded. Otherwise the peak may be considered as valid and the difference in skin conductance values at a zero crossing of the first derivative from negative to positive (peak onset) and a subsequent zero crossing from positive to negative (top) can be considered a the rising edge amplitude or amplitude of the SCR. It should be noted that also long duration slow rises of the skin conductance level may thus be included in the summation of amplitudes.

Figure 4B:
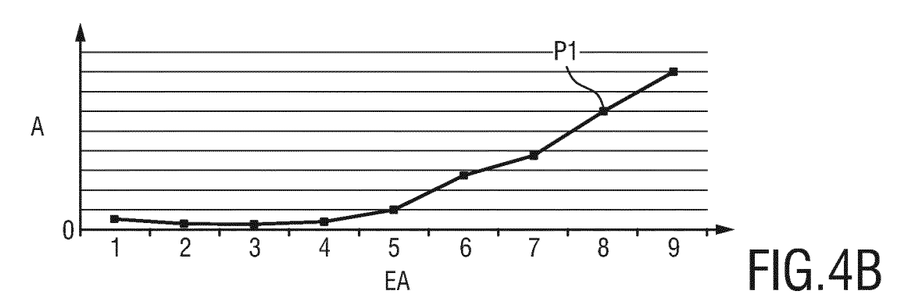
FIG. 4B shows an exemplary graph of sums of rising edge amplitudes indicative of an unhealthy tired state.

FIG. 4B shows a corresponding exemplary graph of the sums of rising edge amplitudes per epoch, wherein the horizontal axis shows the epoch number E # and the vertical axis shows the sum of rising edge amplitudes A for each epoch. The unit of the vertical axis can again be given in micro Siemens [µS]. As shown in FIG. 4B, the respective sums of rising edge amplitudes per epoch increases during the course of the day. In view of this transient behavior during the course of the day, the analysis unit 15 of the proposed signal processing device 10 therefore classifies the user into an 'unhealthy tired' state. A person experiencing this state of fatigue can be bound to be more sensitive to what is happening to them. Such an increased sensitivity may generally result in a more irritable mood. Little annoyances already can cause strong outbursts of anger.

Figure 5A:
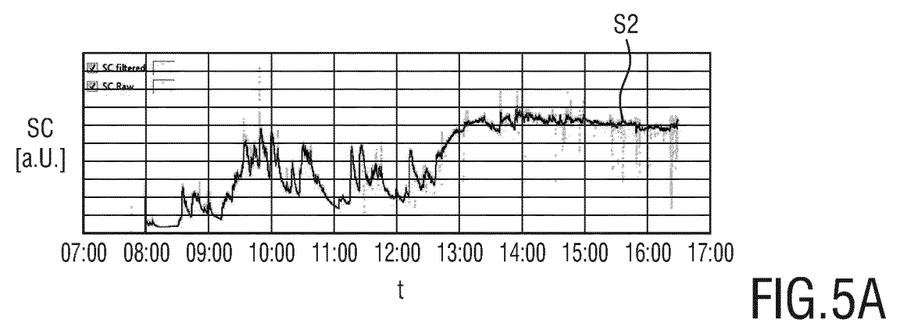
FIG. 5A shows an exemplary skin conductance data signal indicative of a healthy tired state.

FIG. 5A shows a second exemplary skin conductance data signal S2 indicative of an 'healthy tired' state of the user towards the end of the day. Similar to FIG. 4A, the horizontal axis again denotes the time t of the day, whereas the vertical axis denotes the skin conductance SC. The skin conductance data signal S2 in this embodiment represents a working day from about 8:30 AM to 5:00 PM. The data represents the sensor output of a full workday of another driving license examiner. As can be seen from the skin conductance trace S1, a skin conductance peak density, for example the number of peaks per 30 minutes, goes down and also an average peak height decreases at the end of the workday. It has been found that in this pattern, a response to emotional stimuli almost vanished compared to a non-fatigued state earlier the same day. The processing steps for the skin conductance data signal S2 of FIG. 5B corresponds to that of signal S1 in FIG. 5A as described above.

Figure 5B:
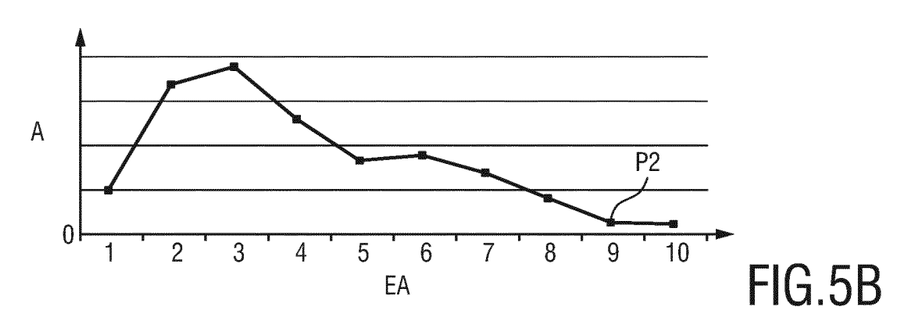
FIG. 5B shows an exemplary graph of sums of rising edge amplitudes indicative of a healthy tired state.

FIG. 5B shows a corresponding exemplary graph of the sums of rising edge amplitudes per epoch, wherein the horizontal axis shows the epoch number E # and the vertical axis shows the sum of rising edge amplitudes A for each epoch. The unit of the vertical axis can again be given in micro Siemens [µS]. As shown in FIG. 5B, the respective sums of rising edge amplitudes per epoch decreases during the course of the day. In view of this transient behavior during the course of the day, the analysis unit 15 of the proposed signal processing device 10 therefore classifies the user into a 'healthy tired' state. As described above, it can be seen as perfectly healthy to show a reduced response to stressors when being tired. The low value of the first data point in FIG. 5B may be attributed to the person still being tired in the morning.

In an embodiment, a decrease of the sum of rising edge amplitudes per epoch may be determined by the analysis unit if the sum of rising edge amplitudes decreases by a predetermined percentage with respect to one or more preceding epochs that are evaluated. For example, a decrease may be determined if the sum of rising edge amplitudes decreases by 25% with respect to an average value of the sum of rising edge amplitudes of the three preceding epochs. Correspondingly, an increase of the sum of rising edge amplitudes per epoch may be determined by the analysis unit if the sum of rising edge amplitudes increases by a predetermined percentage with respect to one or more preceding epochs that are evaluated. For example, an increase may be determined if the sum of rising edge amplitudes increases by 25% with respect to an average value of the sum of rising edge amplitudes of the three preceding epochs. It is to be understood that other percentages or thresholds may be applied.

Figure 6:
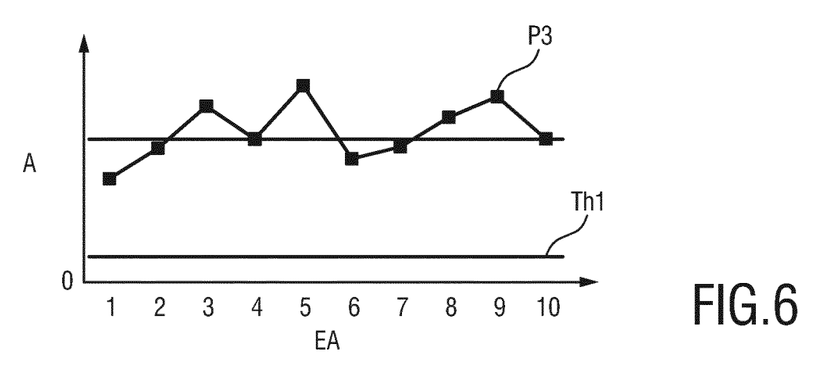
FIG. 6 shows an exemplary graph of sums of rising edge amplitudes indicative of a not tired state.

FIG. 6 shows an exemplary graph of sums of rising edge amplitudes per epoch indicative of a not tired state. As can be seen from the graph, the values constantly exceed the first predetermined threshold Th1. Hence, the user continuously shows a responsiveness to stressors. However, neither a particular increase nor a particular decrease is obvious during the course of the day. In other words, the sum of the rising edge amplitudes per epoch does not deviate by more than a second predetermined value or percentage from an average of the sums of rising edge amplitudes per epoch. In view of this stable behavior during the course of the day and in view that the sum per epoch exceeds the first threshold, the analysis unit 15 of the proposed signal processing device 10 therefore classifies the user into a 'not tired' state.

Figure 7:
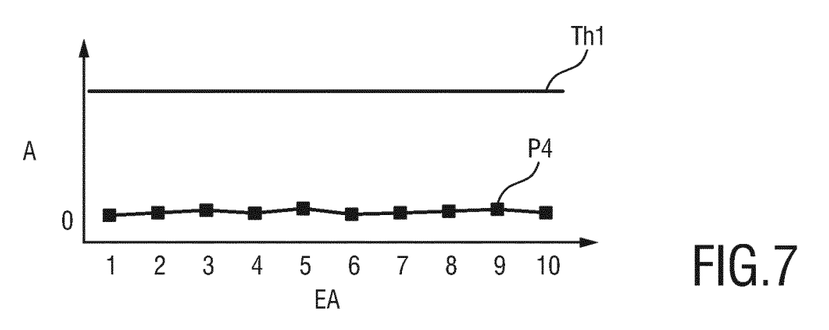
FIG. 7 shows an exemplary graph of sums of rising edge amplitudes indicative of an under-stimulated state.

FIG. 7 shows an exemplary graph of sums of rising edge amplitudes per epoch indicative of an under-stimulated state. As can be seen from the graph, the values remain constantly below the first predetermined threshold Th1. Hence, the user continuously does not show any significant responsiveness to stressors. In view the sum of rising edge amplitudes per epoch remains below the first threshold, the analysis unit 15 of the proposed signal processing device 10 therefore classifies the user into an 'under-stimulated' state. In addition or alternatively, the analysis unit 15 may be configured to classify the user into the under-stimulated state, when an absolute value of the skin conductance level, in particular average value of the skin conductance data signal per epoch, is below a second predetermined threshold, preferably below 0.5 micro Siemens, in particular having a value in the order of 0.1 micro Siemens.

Referring again to FIG. 4A and FIG. 5A, it can be seen that an absolute value of the skin conductance increases over time. In particular, the absolute value may exceed the aforementioned second predetermined threshold. This can be attributed to the fact that a person in a tired state may require an increased effort to do his or her tasks, which may cause an increase in sweating and thus in the skin conductance level. Hence, the analysis unit 15 can be configured to classify the user into a tired state, for example healthy or unhealthy tired, when an absolute value of the skin conductance, in particular average or baseline value of the skin conductance data signal per epoch, increases during the course of the day. The analysis unit 15 may thus also directly be provided with skin conductance data signal from the input unit 11. No such increase is observed for the not tired state or the under-stimulated state. In particular, a setting with little emotional stimuli may result in a low sum of rising edge amplitudes, but also in a significant lowering of the absolute skin conductance level.

Referring again to FIG. 1, the system for improving sleep effectiveness 1 can determine an advice to optimize the sleep effectiveness. In an embodiment, the advice can be determined by the signal processing unit 10 and provided as an output signal via its output unit 16. However, the advice can also be determined by the interface 31 for providing the user with a sleep preparatory advice based on the emotional state of the user as determined by the signal processing unit 10.

For example, for the unhealthy tired state a sleep preparation or wind down period is advised before going to bed. An exemplary sleep preparatory advice can comprise that a period of two hours of low emotional stimuli, accompanied with a relaxing activity is needed to prevent a long sleep onset time, and to improve the amount and length of deep sleep stages, which are especially recuperating. During deep sleep stages parts of the brain switch off, allowing weak links that have been formed that day between nerve cells to disappear. It has been found that the length of the wind down period can be dictated by the time it takes for emotion induced cortisol to be removed from the body. It has been found that the sleep preparatory can advantageously take place in a setting with dimmed light, having a low color temperature. This allows the onset of melatonin production to coincide with bedtime.

If the user has been classified as 'healthy tired' a shorter sleep preparation or wind down for example of 30 minutes duration can be recommended. The setting can be the same or different as described for the unhealthy tired state.

If the user has been classified as 'not tired', for example, only the dimmed low color temperature light setting is recommended. Advantageously, if the person wants to engage in laptop or computer work the use of a color temperature down regulating app can be recommended.

If the user has been classified as being in an 'under-stimulated' state, the user can for example be advised to engage in physical activity, in particular several hours prior to bedtime.

Figure 8:
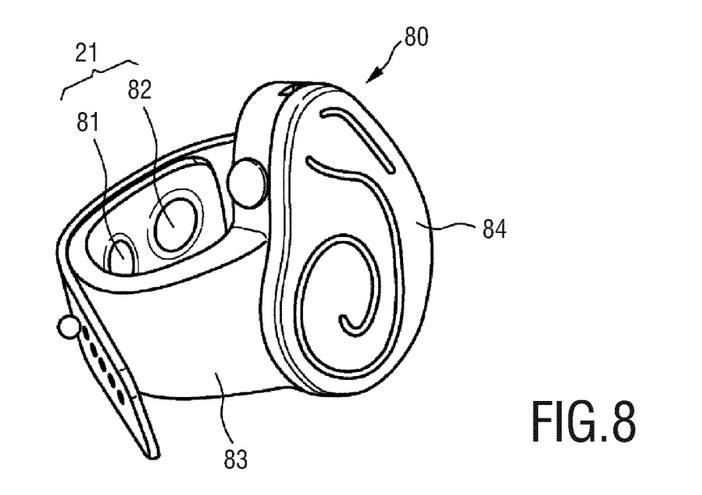
FIG. 8 shows a schematic diagram of an embodiment of a wearable device comprising a skin conductance sensor.

FIG. 8 shows a perspective view of an embodiment of a wearable device 80 comprising a skin conductance sensor in the form of a wristband wearable by a user. The wristband comprises a wristband material part 83 and a casing 84. The wristband material part 83 can loop around the wrist of the user. It will be understood that the wearable device 80 could also be worn around any other suitable body part, such as the ankle, foot or hand, where a skin conductance data signal can be measured.

The wearable device 80 can in particular comprise some or all of the elements of the system 1 for improving sleep effectiveness of a user described herein. For instance, in an embodiment a complete system 1 can be provided in an unobtrusive and wearable format. Alternatively, the wearable device 80 can only comprise the sensor 21 and the other elements of the system 1 are located at a remote location or device (e.g. a remote computer).

At least, the wearable device 80 comprises the skin conductance sensor 21. The skin conductance sensor 21 comprises skin conductance electrodes 81, 82 in combination with a skin conductance measuring unit (not shown). In the embodiment of FIG. 8, two skin conductance electrodes 81, 82 are integrated into the wrist band material part 83. The skin conductance electrodes 81, 82 can be arranged so as to contact the volar side of the wrist, where there is normally not a lot of hair, when the wearable device 80 is put on or worn by the user. In this way, a better measurement of the skin conductance can be provided.

The skin conductance measuring unit can be adapted to measure the skin conductance of the user between the skin conductance electrodes 81, 82. The skin conductance electrodes 81, 82 can be connected to the skin conductance measuring unit by means of wires integrated in the wristband material part 83. In particular, the skin conductance measuring unit or sensor can comprise a voltage generator for applying a voltage between the at least two skin conductance electrodes, a sensing unit for sensing a current between the at least two electrodes, and/or a calculating unit for calculating the skin conductance based on the sensed current. The measured skin conductance over time forms the skin conductance data (or trace). The skin conductance data (or trace) can for example be stored in a memory of the wearable device 80, or can be (e.g. wirelessly) transmitted to an external unit using a (wireless) transmitter.

The skin conductance measuring unit and/or the signal processing device 10 can be integrated into the casing 84 of the wearable device 80. The wearable device 80 can further comprise a transmitter for wirelessly transmitting data over a wireless communication link such as the skin conductance data or an output signal indicative of the emotional state as determined by the signal processing device 10.

Still further, the interface 31 for providing the user with the sleep preparatory advice based on the emotional state of the user can be integrated into the wearable device 80, e.g. in the form of an optical signaling element (e.g. a blinking LED or other signal on a screen), an audible sound emitter emitting an audible warning signal and/or a haptic feedback unit. Alternatively, as shown in FIG. 2 the interface 31 can be a separate part or device such as a smartphone 30, computer or other electronic device to which the signal processor device 10 is able to transmit information. For example, a built-in Bluetooth transceiver can be included in the wearable device.

The wearable device can also have different forms. For instance, it can have the form of a body belt worn by the user or it can be portable and can be clipped to a belt of the user or it can be implemented as a sticker or even a flexfoil that may stick to a part of the user's body.

Figure 9:
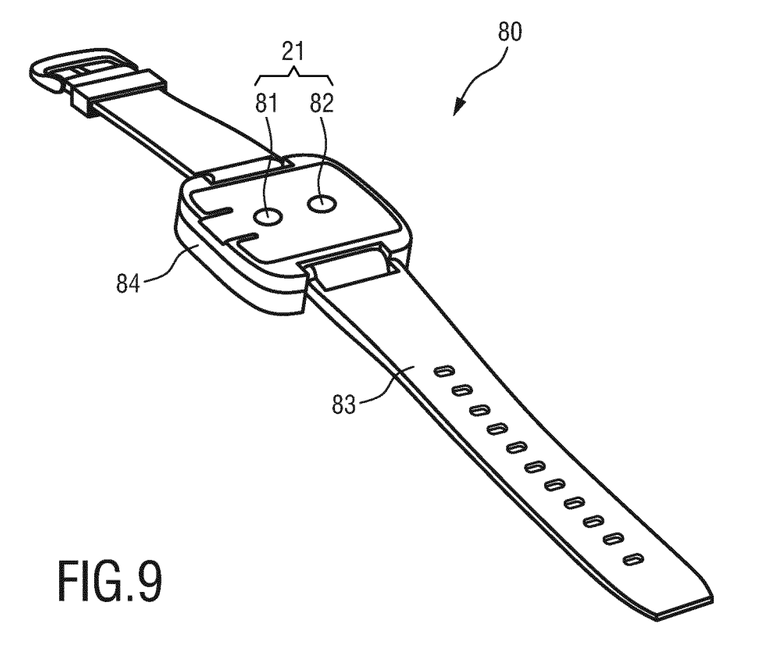
FIG. 9 shows a second schematic diagram of an embodiment of a wearable device comprising a skin conductance sensor.

FIG. 9 shows a second schematic diagram of an embodiment of a wearable device 80 comprising a skin conductance sensor 21. In this embodiment, the electrodes 81, 82 are of the skin conductance sensor 21 are embedded in the casing 84, for example of a smart watch and no longer in the strap as shown in FIG. 8.

Figure 10:
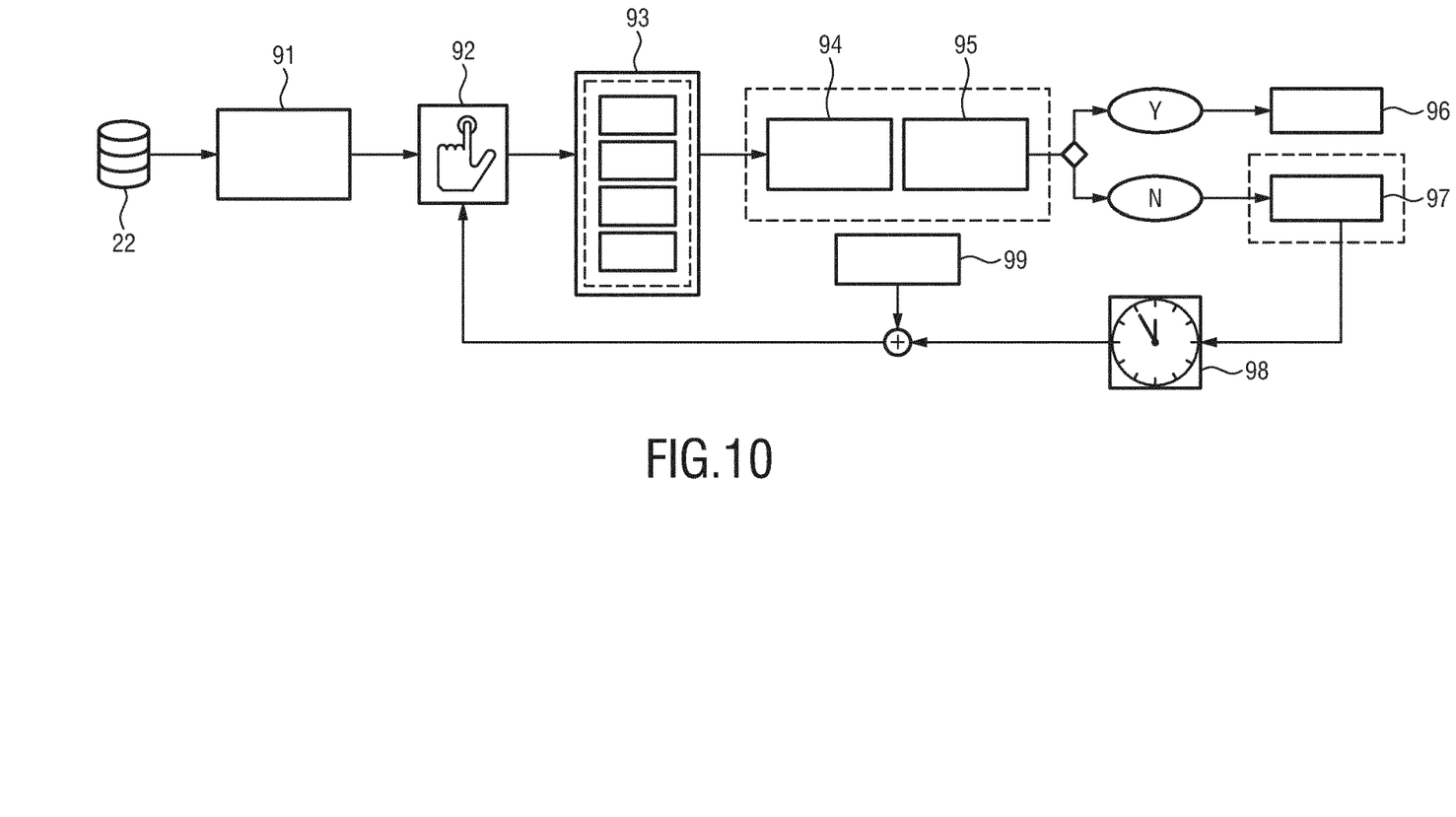
FIG. 10 shows an exemplary flowchart of the concept for improving sleep effectiveness of a user.

FIG. 10 shows an exemplary flowchart of the concept for improving sleep effectiveness of a user. In this embodiment, the signal processing device may be a smartphone comprising program code means for causing the smartphone to carry out the steps of the signal processing method. For example, a coaching app can be provided aimed at preparing a person to fall asleep fast and preferably have a sleep period containing deep-sleep stages.

In this embodiment, the skin conductance data can be provided by a database 22 or for example an external skin conductance sensor device which is couple to the smartphone via Bluetooth. The skin conductance data can be validated and/or a calibration can be performed in an optional step 91. A further optional step 92 in form of a user interaction initiates, for example the execution of an app, initiates the processing of the skin conductance data of the user. Alternatively, the processing can be automatically started at a predetermined time or for example when the skin conductance data of the user becomes available. In a next step 93, the proposed method for processing the skin conductance data of the user is carried out. For example, the user can be classified into one of four emotional states: under-stimulated, not tired, healthy tired or unhealthy tired. Based thereon, the app may convey a notification regarding the emotional state to the user in step 94. In an optional step 95, a sleep readiness of the user can be assessed. If it has been determined that the user is ready to go to sleep, a corresponding message can be provided to the user in step 96. Alternatively, if the user is not yet ready to go to sleep, the app can provide a user notification to the user comprising an action suggestion to the user for sleep preparation in step 97. Optionally, the process can be repeated for example after a predetermined waiting time 98. Advantageously, additional skin conductance data, for example another epoch having a duration of for example 30 minutes can be taken into account then.

Optionally, the processing device 10 can be configured to monitor the effectiveness of the sleep preparation or wind down. For example, the analysis unit 15 may be further configured to monitor a transient behavior of the sum of rising edge amplitudes per unit of time during the sleep preparation. A lowering of the sum of rising edge amplitudes per unit of time can indicate reduced responses or even an absence of responses to stressors, which may be taken as an indicator of successful wind down.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A signal processing device for processing skin conductance data of a user the device comprising:
   an input unit that receives a skin conductance data signal indicative of a skin conductance of the user while the user is awake;
   a segmentation unit that segments the skin conductance data signal into a plurality of epochs, the plurality of epochs having a first epoch and a final epoch;
   a peak detection unit that detects peaks in the skin conductance data signal;
   a calculation unit that calculates a sum of rising edge amplitudes of the detected peaks per epoch;
   an analysis unit that classifies the user into an emotional state based on a transient behavior of the sums of rising edge amplitudes per epoch from the first epoch to the final epoch, wherein the analysis unit is configured to:
      classify the user into an unhealthy tired state when the sum of rising edge amplitudes per epoch increases overall from the first epoch to the final epoch; and
      classify the user into a healthy tired state when the sum of rising edge amplitudes per epoch decreases overall from the first epoch to the final epoch;
      wherein the analysis unit classifies the user into the emotional state based on a comparison the sum of rising edge amplitudes of one or more epochs at or after the first epoch with the sum of rising edge amplitudes of one or more epochs at or before the final epoch;
   and
   an output unit that outputs an output signal indicative of the emotional state.

2. The signal processing device of claim 1, wherein the analysis unit further classifies the user into
   a not tired state when the sum of rising edge amplitudes per epoch remains stable overall from the first epoch to the final epoch and exceeds a first threshold; and/or
   an under-stimulated state of the user when the sum of rising edge amplitudes per epoch remains below the first threshold overall from the first epoch to the final epoch.

3. The signal processing device of claim 1, wherein the skin conductance data signal is indicative of a full workday measurement of the skin conductance of the user.

4. The signal processing device of claim 1, wherein each epoch has a duration between 10 and 90 minutes.

5. The signal processing device of claim 1, wherein each epoch has a duration between 20 and 40 minutes.

6. A system for improving sleep effectiveness of a user, the system comprising:
   a signal processing device for processing skin conductance data of a user, the device comprising:
      an input unit that receives a skin conductance data signal indicative of a skin conductance of the user while the user is awake;
      a segmentation unit that segments the skin conductance data signal into a plurality of epochs;
      a peak detection unit that detects peaks in the skin conductance data signal;
      a calculation unit that calculates a sum of rising edge amplitudes of the detected peaks per epoch;
      an analysis unit that classifies the user into an emotional state based on a transient behavior of the sums of rising edge amplitudes per epoch during the course of a day, wherein the analysis unit is configured to:
         classify the user into an unhealthy tired state when the sum of rising edge amplitudes per epoch increases overall from the first epoch to the final epoch; and
         classify the user into a healthy tired state when the sum of rising edge amplitudes per epoch decreases overall from the first epoch to the final epoch;
         wherein the analysis unit classifies the user into the emotional state based on a comparison the sum of rising edge amplitudes of one or more epochs at or after the first epoch with the sum of rising edge amplitudes of one or more epochs at a final epoch;
      an output unit that outputs an output signal indicative of the emotional state; and
      an interface that provides the user with a sleep preparatory advice based on the emotional state of the user.

7. The system of claim 6, further comprising a skin conductance sensor for measuring skin conductance data of a user.

8. The system of claim 6, wherein the system is at least in part configured as a wearable device.

9. The system of claim 6, wherein the interface provides the sleep preparatory advice to the user a predetermined time interval before bedtime.

10. The system of claim 6, wherein the sleep preparatory advice comprises one or more of a period of low stimuli, a relaxing activity, physical activity, calming music, provision of scents, dimmed lighting, and/or lighting having a low color temperature.

11. The system of claim 6, wherein the system controls one or more of a light source, an audio unit and/or a scent dispenser based on the emotional state of the user.

12. The system of claim 6, wherein the sleep preparatory advice comprises a duration of a recommended wind down period, wherein the duration of the wind down period is determined based on the emotional state of the user.

13. The system of claim 6, further comprising a sleep assessment sensor, wherein the system is configured to adjust the sleep preparatory advice based on a feedback signal from the sleep assessment sensor.

14. The system of claim 6, further configured to provide the sleep preparatory advice to the user at least two hours before bedtime.

15. A non-transitory computer-readable medium comprising computer code that, when executed by a processor, causes the processor to:
   obtain skin conductance data signal indicative of a skin conductance of the user while the user is awake;
   segment the skin conductance data signal into a plurality of epochs, wherein the plurality of epochs comprise a first epoch and a final epoch;
   detect peaks in the skin conductance data signal;
   calculate a sum of rising edge amplitudes of the detected peaks per epoch;
   classify the user into an emotional state based on a transient behavior of the sum of rising edge amplitudes per epoch from the first epoch to the final epoch,
   wherein the user is classified into an unhealthy tired state when the sum of rising edge amplitudes per epoch increases overall from the first epoch to the final epoch; and wherein the user is classified into a healthy tired state when the sum of rising edge amplitudes per epoch decreases overall from the first epoch to the final epoch;

wherein the classifying is based on a comparison the sum of rising edge amplitudes of one or more epochs at or after the first epoch with the sum of rising edge amplitudes of one or more epochs at or before the final epoch.

16. The medium of claim 15, wherein the computer code causes the processor to classify the user into:

a not tired state when the sum of rising edge amplitudes per epoch remains stable overall from the first epoch to the final epoch and exceeds a first threshold; and/or an under-stimulated state of the user when the sum of rising edge amplitudes per epoch remains below the first threshold overall from the first epoch to the final epoch.

17. The medium of claim 15, wherein the skin conductance data signal is indicative of a full workday measurement of the skin conductance of the user.

18. The medium of claim 15, wherein each epoch has a duration between 10 and 90 minutes.

19. The medium of claim 15, wherein the computer code causes the processor to provide the user with a sleep preparatory advice based on the emotional state of the user.

20. The medium of claim 19, wherein the sleep preparatory advice comprises one or more of a period of low stimuli, a relaxing activity, physical activity, calming music, provision of scents, dimmed lighting, and/or lighting having a low color temperature.

* * * * *